United States Patent [19]
> Tipton

[11] 3,972,423
[45] Aug. 3, 1976

[54] APPARATUS FOR HANDLING COVERSLIPS
[75] Inventor: Peter William Tipton, Reading, England
[73] Assignee: John Wyeth & Brother Limited, Maidenhead, England
[22] Filed: Aug. 1, 1974
[21] Appl. No.: 493,592

[30] Foreign Application Priority Data
Aug. 16, 1973 United Kingdom............... 38702/73

[52] U.S. Cl. ........................... 214/1 BT; 214/8.5 F; 198/20 R; 222/575; 294/64 A
[51] Int. Cl.² ......................................... B65G 61/00
[58] Field of Search............. 214/1 BS, 1 BT, 1 BH, 214/1 BV, 1 R, 1 BE, 8.5 D, 6 ES, 8.5 F; 294/64 R, 64 A, 64 B, 65; 198/20 R

[56] References Cited
UNITED STATES PATENTS
| | | | |
|---|---|---|---|
| 805,887 | 11/1905 | Smith............................ | 294/64 R X |
| 824,920 | 7/1906 | Erickson...................... | 214/1 BT X |
| 2,247,787 | 7/1941 | Schmidt............................ | 214/1 BT |

*Primary Examiner*—Frank E. Werner
*Attorney, Agent, or Firm*—Joseph Martin Weigman

[57] ABSTRACT

A method for transferring a coverslip from one location to another comprises placing a suction pad on to one surface of the coverslip, applying suction to the suction pad so that the coverslip adheres temporarily to the suction pad and transferring the suction pad with the adhering coverslip from a first location to a second location. The invention also provides a specific apparatus for carrying out the method. Also provided is an apparatus for feeding coverslips singly from a stack of coverslips employing an open bottomed hopper for the stack of coverslips which rests on a plate having a depression, to accommodate a single coverslip, in its upper surface. The invention further provides a substantially automatic apparatus for placing mounting medium and coverslips on to microscope slides which apparatus can include the apparatus for transferring coverslips and the apparatus for feeding coverslips singly from a stack of coverslips.

2 Claims, 12 Drawing Figures

APPARATUS FOR HANDLING COVERSLIPS

This invention relates to a method and apparatus for handling coverslips.

Laboratories such as histological laboratories prepare a considerable number of microscopic slides for subsequent viewing under a microscope. In the preparation of such slides the object to be viewed, for example a histological section or a cytological or haematological smear, is first placed on the slide and usually treated with one or more dyes; a small amount of mounting medium is next placed on the object and finally a coverslip or cover glass is placed on top of the mounting medium. The placing of the mounting medium and coverslip on the slide are time consuming operations when a large number of slides have to be prepared by hand. Coverslips are normally sold in packs containing a stack of coverslips and it is necessary to separate coverslips from the stack and deposit them singly on the mounting medium on the slide.

Accordingly, the present invention provides a method of transferring a coverslip from one location to another which comprises placing a suction pad on to one surface of the coverslip, applying suction to the suction pad so that the coverslip adheres temporarily to the suction pad and transferring the suction pad with the adhering coverslip from a first location to a second location.

The method of the invention is particularly applicable for transferring a coverslip on to a slide. When the coverslip is at the second location, e.g. on the slide, it may be removed from the suction pad by applying pressure to the surface of the coverslip adhering to the suction pad.

The invention further provides an apparatus which may be used for carrying out the above described method of the invention. According to this aspect of the invention, an apparatus for transferring a coverslip from one location to another comprises a suction pad, means for bringing the suction pad into contact with one surface of the coverslip, means for applying suction to the suction pad when the pad is in contact with the surface of the coverslip and means adapted to move the suction pad from a first location to a second location.

The apparatus, preferably, includes means for removing the coverslip from the suction pad when the coverslip is at the second location, e.g. on the slide. The means for applying suction to the suction pad and for removing the coverslip from the suction pad can comprise an elastic compressible bulb, e.g. a rubber teat, connected by tubing to the suction pad such that when the bulb is compressed air is forced out of the suction pad and when the bulb is released air is drawn into the suction pad. The movement of the suction pad is preferably arranged so that when the suction pad is in contact with the surface of the coverslip at the first location the pressure on the compressed bulb is released so applying suction to the suction pad and when the pad is at the second location the bulb is compressed so forcing air out of the suction pad and hence releasing any coverslip adhering to the pad.

The apparatus for transferring a coverslip from one location to another is particularly useful for transferring a single coverslip on to a slide. The single coverslip may be separated from a stack of coverslips by another aspect of the present invention. According to this aspect of the invention, an apparatus for feeding coverslips singly from a stack of coverslips comprises an open bottomed hopper for the stack of coverslips, a plate containing a depression in its upper surface, the depth and size of the depression being such that only a single coverslip can enter the depression at any one time and the hopper being adapted to be mounted with its open bottom end resting on the upper surface of the plate, and means for moving the hopper and plate relative to each other such that when the depression is below the stack of coverslips, the bottom coverslip of the stack can enter the depression. When the coverslip is in the depression the plate may be moved relative to the hopper so that the hopper is still mounted on the plate but a single coverslip remains in the depression and hence is removed from the bottom of the stack. When the depression is clear of the open-ended bottom of the hopper, the coverslip may be removed from the depression, e.g. by the apparatus, hereinabove described, for transferring a coverslip from one location to another.

Preferably the hopper remains stationary and means are provided for moving the plate relative to the hopper.

According to a further aspect of the invention there is provided a substantially automatic apparatus for placing mounting medium and coverslips on to microscope slides said apparatus comprising a conveyor adapted to carry microscope slides, a first station positioned at a first location on the conveyor and comprising means to align a slide on the conveyor, a second station positioned at a second location on the conveyor and comprising means to place mounting medium on the aligned slide, a third station positioned at a third location on the conveyor and comprising means adapted to place a coverslip from a stack of coverslips on to the mounting medium on the slide and means for stopping the conveyor when the slide is at each of the three stations.

The means to place a coverslip from a stack of coverslips on to the mounting medium on the slide preferably comprises a combination of the apparatus for feeding coverslips singly from a stack of coverslips and the apparatus for transferring a coverslip from one location to another as hereinbefore described.

A preferred embodiment of the invention will now be described with reference to the accompanying drawings in which.

(In certain of the figures various parts of the machine have been omitted or shown 'broken' for clarity of illustration)

As shown in the drawings the preferred embodiment of the apparatus of the present invention comprises a framework 10 comprising a plurality of strips which support the other components of the apparatus. Supported on the framework there are three conveyors 11, 12 and 13.

Conveyor 11 may be termed "the input conveyor" and it comprises a pair of parallel endless metal chains 14 and 14a, the upper travels of which are supported on a corresponding pair of parallel metal runners 15 and 15a. The distance between the runners 15 and 15a is slightly less than the length of a microscope slide so that a slide placed across the two chains 14 and 14a is supported near its ends.

Figure 2:
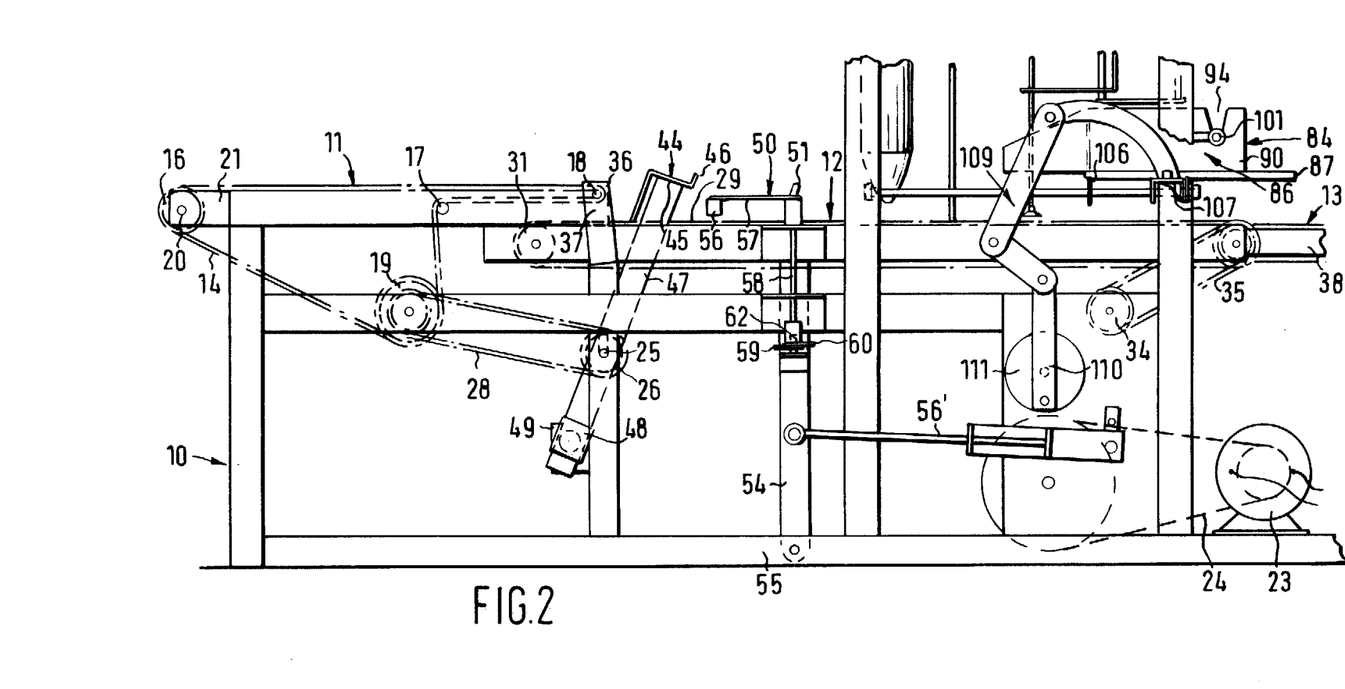
FIG. 2 is an enlarged side elevation of part of the machine shown in FIG. 1.

The endless chains 14 and 14a pass over a pair of idler sprockets 16, 16a, a supporting rod 17, a pair of short supporting rods 18, 18a and a pair of driven sprockets (one of which, 19, is shown in FIG. 2). The idler sprockets 16, 16a are on axle 20, supported in strips 21, 21a attached to the runners 15, 15a. The supporting rods 17, 18 and 18a are attached to the framework 10. The driven sprockets are on common axle 22 which is driven from a motor 23 via the chain drive 24 acting via gear coupling (not shown) on a single-throw crankshaft 25 carrying a sprocket 26; the axle 22 carries a sprocket 27 which is driven by a chain 28 from the sprocket 26.

Conveyor 12 may be termed "the process conveyor" and it comprises a pair of endless metal chains 29, 29a, the upper travels of which are supported by a corresponding pair of metal runners 30, 30a. The distance between the chains 29 and 29a is similar to the distance between the chains 14 and 14a. The endless chains 29, 29a pass over a pair of idler sprockets (one of which, 31 is shown in FIG. 2) and a pair of driven sprockets 32, 32a. The sprockets 32, 32a are mounted on a common axle 33 which is driven from a sprocket 34 via the chain drive 35. The sprocket 34 is driven intermittently by a form of Geneva wheel mechanism and gears (not shown) from the motor 23.

Between the input conveyor 11 and the process conveyor 12 is a pair of L-shaped stop members 36, 36a, mounted on strips 37, 37a attached to the framework 10. The strips 37, 37a also carry the short supporting rods 18, 18a. The stop members 36, 36a are sufficiently high to prevent slides on the conveyor 11 passing directly on to conveyor 12.

Conveyor 13 may be termed the "output conveyor". It comprises a pair of parallel endless metal chains 38, 38a, the upper travels of which are supported by a corresponding pair of parallel metal runners 39, 39a. The distance between the parallel chains 38 and 38a is slightly less than the distance between the chains 29, 29a of process conveyor 12. The chains 38, 38a pass over idlers 40, 40a which are mounted on the same axle 33 as the driven sprockets 32, 32a of the process conveyor 12. The chains 38, 38a also pass over a pair of driven sprockets 41 mounted on an axle 42 carried between extensions of the runners 39, 39a. The axle 42 is driven by the chain drive 43 which itself is driven from the motor 23 by gearing (not shown).

The slides are transferred from the input conveyor 11 to the process conveyor 12 by a slide transfer mechanism 44. The slide transfer mechanism 44 comprises a platform 45 having an upturned edge 46. The platform 45 is mounted on top of a strip 47. The strip 47 is supported near the middle of its length by the single throw crankshaft 25. The lower end of the strip 47 passes through a slide member 48 which is pivotally mounted on an extension 49 of the framework 10 such that it is freely rotatable. The motor 19 drives the crankshaft 25 so that the platform 45 moves in an elliptical path. The platform 45 is driven in a clockwise direction, as viewed in FIGS. 1 and 2 such that any slide on conveyor 11 abutting the stops 36, 36a is lifted on to the platform 45 on its upward path. On the continuation of the platform's upward path, the slide is lifted off the conveyor 11 as platform passes up between the chains 14, 14a and then over the stops 36, 36a. The platform 45 then proceeds on its downward path depositing the slide on to the conveyor 12 as the platform passes down between the pair of chains 29, 29a.

The first station on the process conveyor is a slide aligning mechanism 50. The slide aligning mechanism 50 ensures that the long axis of the slide is at right angles to the conveyor 12 and that the slide is centrally positioned on the conveyor.

The means for ensuring that the long axis of the slide is at right angles to the conveyor comprises a pair of fingers 51, 51a mounted on a shaft 52 carried on the frame 10. The shaft 52 is adapted to be revolved approximately a quarter revolution in each direction such that the fingers 51, 51a move from a substantially horizontal position to a vertical position (as shown in FIG. 2) and back again. In moving to the vertical position, the fingers move upwards between the chains 30, 30a so contacting the leading long edge of any slide located at the first station on the process conveyor 12. Also mounted on the shaft 52 are two fingers 53, 53a pointing substantially downwards. A rocking frame 54 is pivotally mounted near its bottom on a lower member 55 of the frame 10. The rocking frame is rocked to and fro by means of shaft 56' driven via gearing by the motor 23. Attached to the top of the frame is a horizontal bar which contacts alternatively finger 53 and finger 53a as the frame 54 rocks so causing the oscillating motion of the shaft 52.

Figure 4:
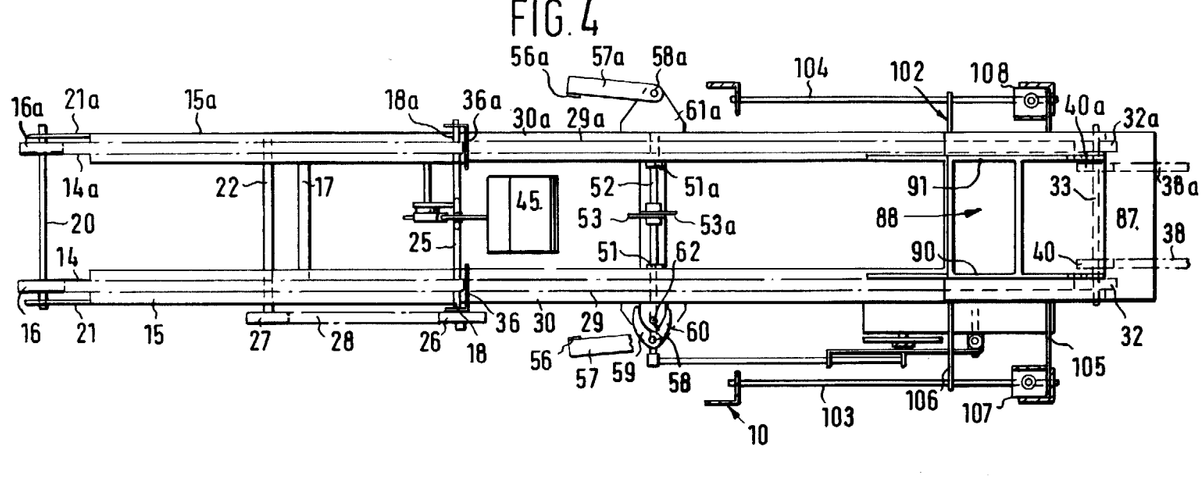
FIG. 4 is a plan view, viewed from above, of that part of the machine shown in FIG. 2.

The means for ensuring that the slide is centrally positioned on the process conveyor comprises a pair of fingers 56, 56a mounted on strips 57, 57a. The strips 57, 57a are pivotally mounted on rods 58, 58a. Also mounted on the rods 58, 58a near the bottom are two pairs of levers 59, 59a and 60, 60a (59a and 60a correspond to 59 and 60 but they are not illustrated in the figures; in FIG. 4 they are hidden by the support 61a for the rod 58a). A pair of short upstanding rods (one of which, 62 is shown in FIG. 2) are attached to either side of the rocking frame 54 and positioned between each pair of levers. Intermittent rocking movement of the frame 54 causes the short upstanding rods to contact intermittently levers 59, 59a or 60, 60a so causing intermittent partial rotation of the rods 58, 58a first in one direction then the other. When rod 58 rotates clockwise and rod 58a anticlockwise (as viewed in FIG. 4) the strips 57 and 57a move towards the conveyor 12 causing the fingers 56 and 56a to contact a side edge of any slide located at the first station on the process conveyor. Opposite rotation of the rods 58, 58a results in the two strips 57, 57a moving away from the conveyor 12.

The fingers 51, 51a contact the leading long edge of a slide located at the first station at substantially the same time as the fingers 56, 56a contact one or other of the side edges.

The second station on the process conveyor 12 is a mounting medium applicator 63. The applicator comprises a pipette 64 mounted by means of mounting clips 65, 66 on the framework 10. Mounting medium is placed in the pipette 64. The upper end of the pipette is closed by a rubber bulb 67 which is held against the framework 10. A drop of the mounting medium is delivered from the bottom end of the pipette on to any slide located at the second station by pressure on the bulb 67. Pressure is transmitted from the motor 23 by means of the cogs 68, 69 which cause rotation of the horizontal shaft 70. Mounted on the shaft 70 is a wheel 71 carrying an offset pin 72. Mounted above the pin 72 for reciprocating motion is a push rod 73. The rod is attached to one arm of a pivotally mounted L-piece 74 at its upper end and carries a stud 75 at its lower end. Each revolution of the shaft 70 causes the pin 72 to contact the stud 75 resulting in upward movement of the rod 73 and hence movement of the L-shaped member 74 about its pivot 76. Attached to the upright arm of the L-shaped member is a short horizontal bar 77. Pivotal movement of the L-shaped member 74 causes the bar 77 to contact a longer bar 78, attached to a rotatable shaft 79. Movement of the bar 78 causes partial rotation of the shaft 79. Also attached to the shaft 79 is a screw collar 80 through which passes a screw threaded shaft 81. One end of the shaft 81 carries a pressure pad 82. The distance between the collar 80 and the pressure pad 82 can be adjusted by means of an adjusting wheel 83. Rotation of the shaft 79 results in movement of the shaft 81 with the collar 80 towards the bulb 67 thus causing the bulb to be squeezed by the pressure pad 82. The movement of the shaft 81 is synchronised with the movement of the process conveyor 12 so that when any slide is stationary at the second station the pressure pad 82 squeezes the bulb 67. The pressure on the bar 78 is then released so allowing the bulb 67 to return to its original shape. The amount of pressure transmitted to the pressure pad 82 and hence the volume of mounting medium delivered to the microscope slide can be varied by turning the wheel 83 on the shaft 81 so varying the relative positions of the pad 82 and the threaded collar 80.

The third station at the process conveyor 12 comprises means for transferring a coverslip from a stack of coverslips on to a slide positioned on the conveyor. The means comprises two inter-related mechanisms i.e. a coverslip separator 84 and a coverslip applicator 85.

Figures 8A, 8B:
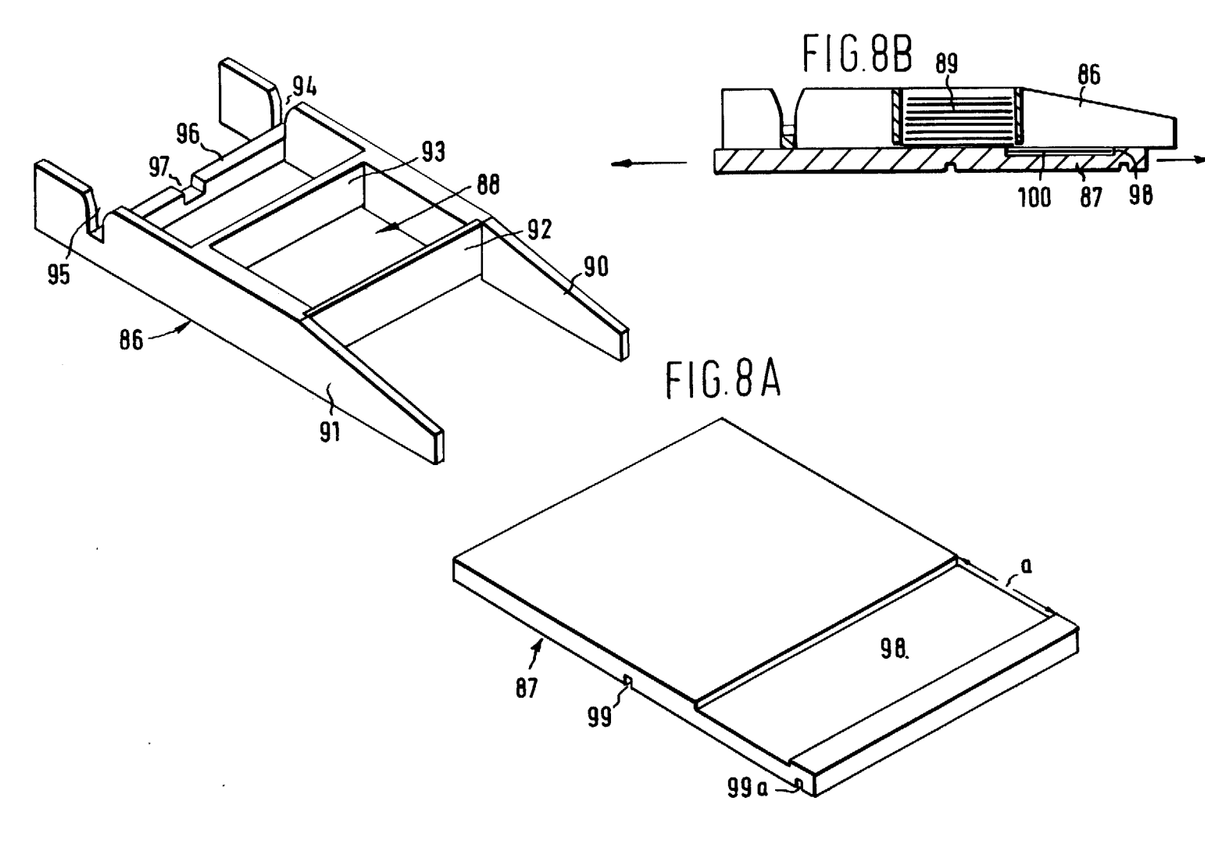
FIG. 8A is an enlarged perspective view of the hopper and associated plate shown (on a smaller scale) in FIG. 1.
FIG. 8B is a vertical cross section of the hopper on top of the plate.

As best seen in FIGS. 8A and 8B the coverslip separator 84 comprises a hopper 86 and a base plate 87. The hopper 86 comprises a rectangular central portion 88 of such dimensions that it can contain a stack of coverslips 89. The hopper 86 has two side pieces 90 and 91 which rest on the upper surface of the base plate 87. The rectangular central position is bounded by the two side pieces 90, 91 and two cross pieces 92, 93. The cross pieces 92, 93 are just clear of the surface of the base plate 87 when the side pieces 90 and 91 are resting on it. The side pieces 90 and 91 have locating slots 94, 95 near their rear ends and are joined by a further cross member 96 having a locating slot 97 near its centre.

The base plate 87 contains a depression 98 in its upper surface. The depth of the depression is substantially the thickness of a single coverslip and the width of the depression, shown by a in FIG. 8A is substantially the same as the width of the coverslip. The length of the depression may be longer than the length of the coverslip so that coverslips of various lengths may be accomodated in the depression; different hoppers are used for coverslips of different lengths, the cross sectional area of the central portion 88 being approximately the same size as the coverslip being used.

The undersurface of the base plate 87 has two parallel groves 99, 99a in it.

In use, the hopper 86 is maintained stationary and the base plate reciprocates as shown by the arrows in FIG. 8B. Each time the empty depression 98 passes under the stack of coverslips 89 the bottom member of the stack falls into the depression and is removed from the stack when the base plate moves its position. When clear of the front cross member 92, a coverslip 100 in the depression 98 may be removed by the coverslip applicator described below.

As shown in FIG. 2, the hopper 86 is kept in a stationary position relative to the framework 10 by means of a removable cross rod 101, attached to the framework, which passes through the locating slots 94, 95. Positioned centrally on the cross rod 101 is a collar which enters the locating slot 97 on cross member 96; this serves to position the hopper centrally. The base plate rests on a framework 102 (FIG. 4) adapted to be moved to and fro along a pair of rods 103, 104 parallel to the conveyor 12. The base plate 87 is located on the framework 102 by the grooves 99 and 99a on the undersurface of the base plate being retained on cross members 105 and 106 of the framework 102. The framework 102, and hence the base plate 87 is pushed to and fro along the rods 103, 104 by a pair of slides 107, 108. As may be seen in FIG. 2, the slides 107, 108 are driven to and fro along the rods 103, 104 by a system of cranks and levers 109, the bottom member of which 110 is eccentrically mounted, for alternating rectilinear motion, on a wheel 111 driven by the motor 23. The drive is so arranged that the framework 102 is stationary at the beginning of each stroke of the slides 107, 108. Hence the movement of the base plate 87 is intermittent.

Figure 3:
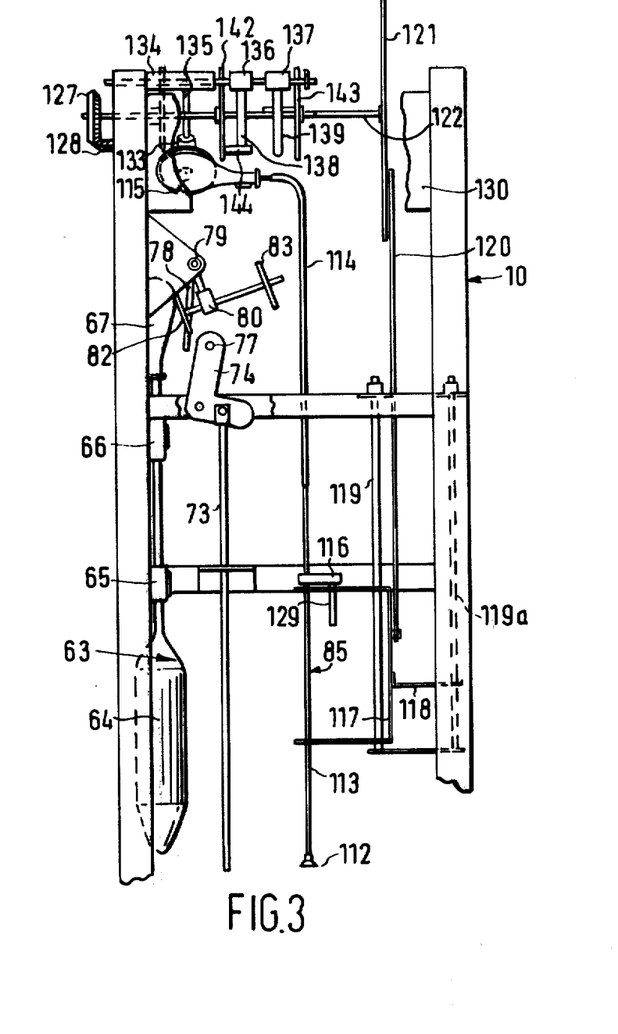
FIG. 3 is an enlarged side elevation of another part of the machine shown in FIG. 1.
Figure 5:
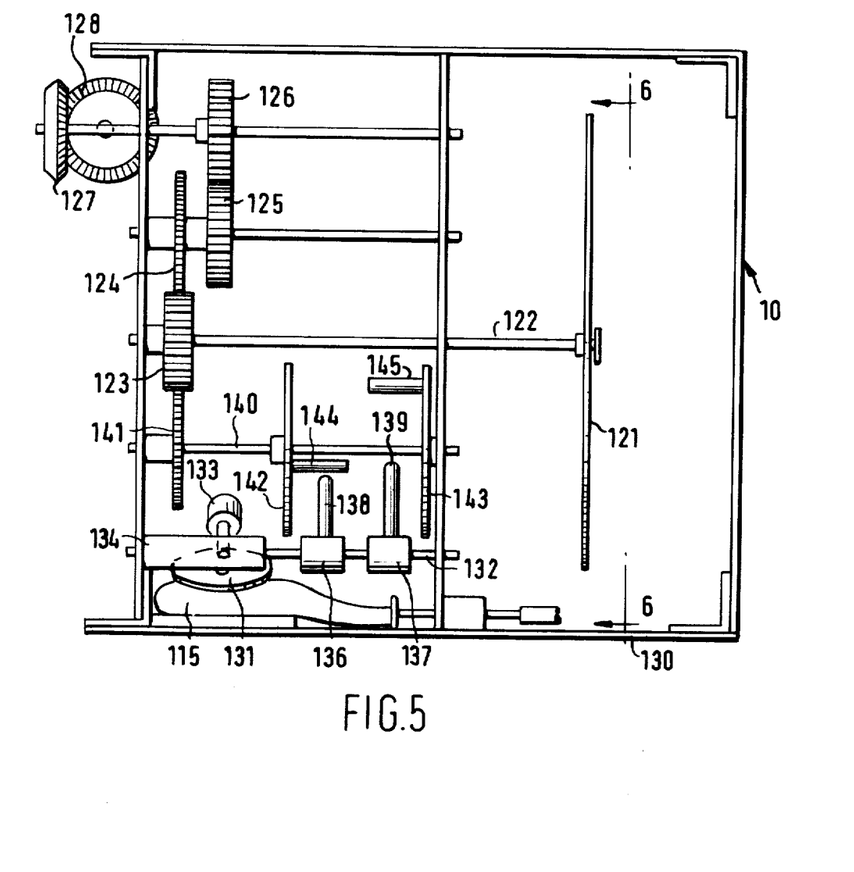
FIG. 5 is a plan view, viewed from above, of that part of the machine shown in FIG. 3.
Figures 6, 7:
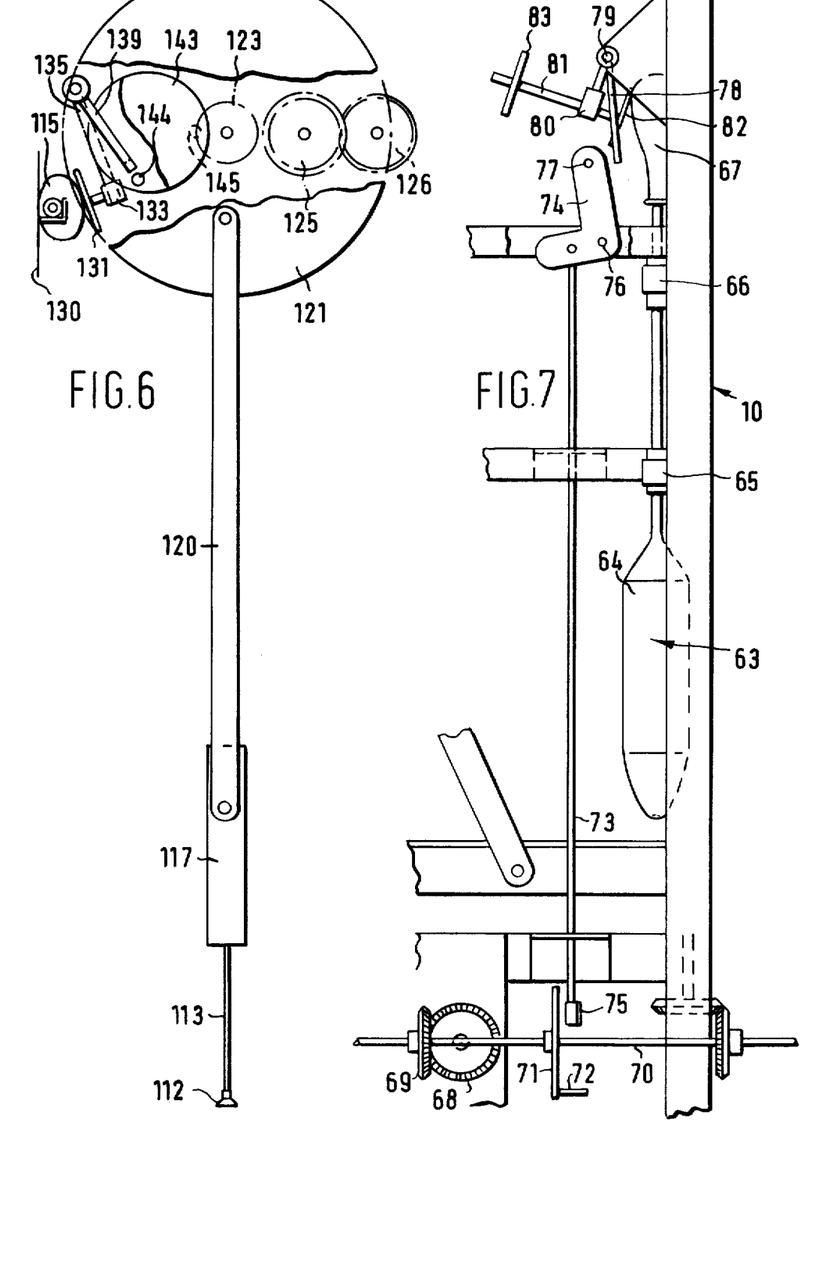
FIG. 6 is an end elevation of part of the machine as viewed along lines 6—6 of FIG. 5.
FIG. 7 is a side elevation of part of the machine shown in FIG. 3 but viewed from the other side.

The coverslip applicator 85 (FIGS. 3 and 6) comprises a rubber suction pad 112 comprising a hollow hemi-spherical sucker. The interior of the pad 112 is connected via a pipe 113 and flexible tubing 114 to a rubber bulb 115. The suction pad 112 may be raised or lowered by raising or lowering a collar 116 mounted on the pipe 113. The pipe 113 passes through, and is free to slide vertically in, a U-shaped member 117. Each arm of the U-shaped member 117 has a hole in it through which passes a vertical guide rod 119. The U-shaped member 117 is driven up and down the guide rod 119 by means of a connecting rod 120 attached to a crank wheel 121. The U-shaped member 117 has an extension piece 118 having a hole in it through which passes a second vertical guide rod 119a so preventing rotation of the U-shaped member 117. As is best seen in FIG. 5, the crank wheel 121 is mounted on a drive shaft 122 which is driven from the motor 23 via gearing 123, 124, 125, 126, 127, 128 (and others not shown). Rotation of the crank wheel 121 causes reciprocating movement of the U-shaped member 117 and hence raising and lowering of the suction pad 112. Rotation of suction pad 112 during its up and down travel is prevented by the short arm 129, mounted on the collar 116, which passes freely through a hole in the upper arm of the U-shaped member 117.

The bulb 115 is retained against a cross-member 130 of the frame 10 and can be squeezed by movement of a pressure pad 131. The pressure pad 131 is mounted on a freely rotatable shaft 132 via connectors 133, 134 and rod 135. Also mounted on shaft 132 are two collars 136, 137 with protruding pins 138, 139, respectively. Adjacent freely rotatable shaft 132 is shaft 140 which is driven by gear 141 engaging with gear 123 on shaft 122. Mounted on shaft 140 are two fixed wheels 142, 143 carrying offset pins 144, 145, respectively. Rotation of the shaft 140 results in pin 144 contacting pin 138 for a short time so causing rotation of shaft 132 and hence pressure of the pressure pad 131 on the bulb 115 followed by a sharp release of the pressure when the pins 144 and 138 are no longer in contact. Further rotation of the shaft 140 results in pin 145 contacting pin 139 for a longer time resulting in a more prolonged pressure by the pressure pad 131 on the bulb 115.

Figure 9A:
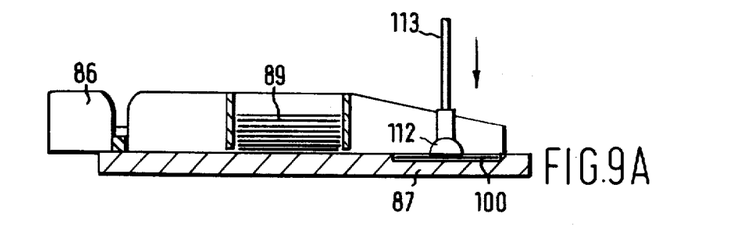
FIGS. 9A, 9B and 9C are cross sectional views of the hopper and plate similar to the view shown in FIG. 8B except that here the hopper and plate are shown in varying relationships to each other and to the suction pad of the coverslip lifting mechanism.
Figure 9B:
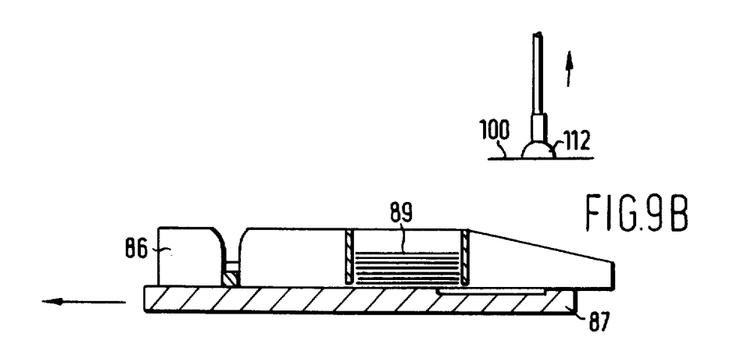
Figure 9C:
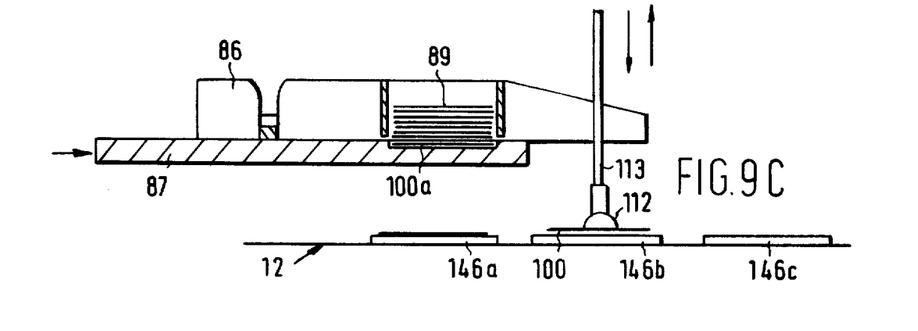

The co-operation of the coverslip separator and the coverslip applicator is illustrated in FIGS. 9A, 9B and 9C. In the position indicated in FIG. 9A a coverslip 100 is in the depression in the base plate 87 and the suction pad 112 is lowered on to the upper surface of the coverslip. The bulb 115 connected to the pad 112 is squeezed and sharply released by the mechanism described above. This causes suction at the suction pad 112 and the coverslip 100 is picked up by the pad 112. The pad 112 is then raised, as shown in FIG. 9B, so withdrawing the coverslip 100 out of the depression in the base plate 87. At the same time as the pad 112 is raised the base plate 87 is withdrawn in the direction of the left hand arrow in FIG. 9B. When the depression is below the stack 89, the pad 112 with the attached coverslip 100 is lowered between the side arms 90 and 91 (FIG. 4) of the hopper 86 as shown in FIG. 9C. The pad 112 is lowered so that the coverslip rests on top of the mounting medium on one (146b) of the slides 146a, 146b and 146c on conveyor 12. When in position the bulb 115 connected to the pad 112 is subjected to prolonged pressure, by the mechanism described above, thus causing the coverslip to be released. A new coverslip 100a enters the depression in the base plate 87. The pad 112 is raised, the base plate moved in the direction of the left hand arrow in FIG. 9C and the pad 112 again lowered so that the components are again in the position indicated in FIG. 9A. The cycle is then repeated.

Figure 1:
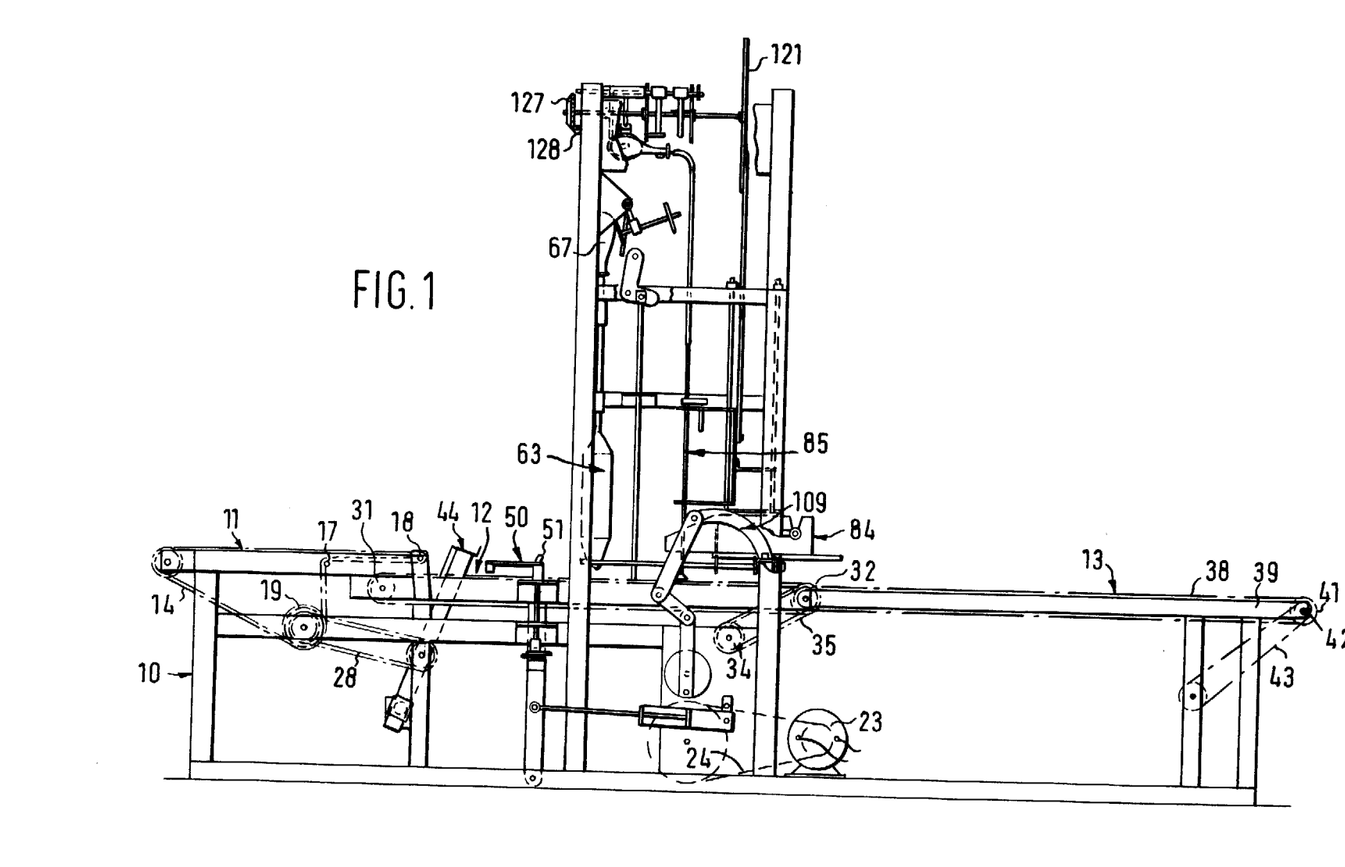
FIG. 1 is a side elevation of a machine embodying the invention.

The drive to the various components of the apparatus shown in FIG. 1 is arranged so that the input conveyor 11 and the output conveyor 12 are driven continuously. The output conveyor is driven relatively slowly. The slide transfer mechanism 44 is driven so that it makes one complete revolution during each complete cycle of the whole apparatus. The process conveyor 12 is driven faster than the output conveyor 13 but intermittently so that a slide placed on the conveyor by the slide transfer mechanism 44 stops three times during its path on the conveyor; once at the slide aligning mechanism 50, once at the mounting medium applicator 63 and once at the coverslip applicator 85.

In use, an operator places slides, having the object to be viewed on their upper surfaces, on the input conveyor 11. The chains 14 and 14a carry the slides forward so that the slides are pushed together with their longitudinal edges touching and the leading longitudinal edge of the leading slide up against the stops 36 and 36a. The leading slide is then picked up on the platform 45 of the slide transfer mechanism 44 and transferred to the process conveyor 12. The slide is then carried along by the chains 29 and 29a until it stops at the slide aligning mechanism 50. The fingers 56, 56a and 53, 53a of the slide aligning mechanism then contact the slide to align it centrally and at right angles to the conveyor 12. The conveyor 12 then restarts and carries the slide to the mounting medium applicator 63. When the slide is positioned under the pipette 64 the conveyor 12 stops automatically and the bulb 67 is squeezed so that a drop of mounting medium is placed upon the object on the slide. The conveyor 12 then restarts and the slide is carried to the coverslip applicator 85. Once the slide is positioned underneath the pad 112 the conveyor 12 stops. A coverslip is transferred by the pad 112 to a position on top of the mounting medium on the slide. The coverslip is then released on to the mounting medium by pressure on the bulb 115 by the pressure pad 131. The conveyor 12 then restarts and the slide with its accompanying coverslip is carried to the right hand end of the conveyor 12 (as viewed in FIG. 1). The slide is then automatically transferred to the slower moving output conveyor 13. The prepared slides are then removed from the output conveyor 13 by an operator.

I claim:

1. In an apparatus for preparing specimen-containing slides for viewing under a microscope by placing a mounting medium over the specimen and a coverslip over the mounting medium, the improvement for transfering a coverslip from a first location to a second location comprising:
   A. A rigid supporting frame;
   B. A compressible bulb fixedly connected to said frame;
   C. Flexible tubing connected to said bulb;
   D. A rigid pipe connected to said tubing;
   E. A suction pad connected to said pipe;
   F. Reciprocating means to raise and lower said pipe and said suction pad in a linear path from a first position in contact with said coverslip to a second position in contact with said slide; and
   G. First compression means supported from said frame and adapted to compress said bulb just prior to contact of said suction pad with said coverslip, and to remove compression while said suction pad and said coverslip are engaged thereby retaining said coverslip in contact with said suction pad.

2. Apparatus as described in claim 1 further comprising a means to deposit said coverslip on a mounting medium which comprises;
   A. A second compression means supported from said frame and adapted to compress said bulb after said coverslip is in contact with the mounting medium on the slide, thereby disengaging said coverslip from said suction pad.

* * * * *